United States Patent

Zombo et al.

[19]

[11] Patent Number: 6,005,913
[45] Date of Patent: *Dec. 21, 1999

[54] SYSTEM AND METHOD FOR USING X-RAY DIFFRACTION TO DETECT SUBSURFACE CRYSTALLOGRAPHIC STRUCTURE

[75] Inventors: Paul John Zombo, Cocoa; Der-Yan Frank Roan, Maitland, both of Fla.

[73] Assignee: Siemens Westinghouse Power Corporation, Orlando, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/625,350

[22] Filed: Apr. 1, 1996

[51] Int. Cl.[6] .................................................. G01N 23/20
[52] U.S. Cl. ............................................. 378/71; 378/73
[58] Field of Search .......................................... 378/71, 73

[56] References Cited

U.S. PATENT DOCUMENTS

| | | | |
|---|---|---|---|
| 4,696,024 | 9/1987 | Pesch | 378/71 |
| 4,910,758 | 3/1990 | Herrick | 378/71 |
| 5,491,738 | 2/1996 | Blake et al. | 378/71 |

FOREIGN PATENT DOCUMENTS

| | | |
|---|---|---|
| 0234538A | 2/1987 | European Pat. Off. . |
| 2166630A | 8/1986 | United Kingdom . |
| 2288961A | 1/1995 | United Kingdom . |

OTHER PUBLICATIONS

Will Kleber, "Einführung in die Kristallographie", *VEB Verlag Technik*, 11th Edition, pp. 335, 336, Berlin DE.

Green, Jr., Robert E., "X–Ray Diffraction Imaging and Analysis," Presented at American Society of Nondestructive Testing, Fall Conference, 1995.

Fitting, D.W. et al., "Real–Time Sensing of Metal Solidification Using Transmission X–Ray Diffraction," Contribution of National Institute of Standards and Technology.

*Primary Examiner*—Craig E. Church

[57] ABSTRACT

A system with three parts: a testing apparatus, a computer system, and a communications line between the two. The testing apparatus has a device that emits x-rays into the sample, a device to position the sample relative to the x-rays and an electro-optical x-ray detector for detecting diffracted x-rays. The computer system has a computer, a computer program, a storage device, a database, and monitor or other means of announcing the results of a test. The computer program directs the computer to accept data from the sample testing system concerning the relationships of the devices, the x-rays, and diffracted x-rays. The computer program also directs the computer to compare this data with a database of previously determined relationships and possible diffraction patterns stored in the storage device. Based on the comparison, the computer program directs the computer to announce the results of the comparison via the monitor or other means, thereby revealing the crystallographic grain structures of the sample. The method encompasses positioning the sample in a path of x-rays projecting from an x-ray means, detecting x-rays that are diffracted by the sample with an electro-optical detector, analyzing the data and announcing the crystallographic grain structures of the sample based on the analyzing step.

18 Claims, 4 Drawing Sheets

SYSTEM AND METHOD FOR USING X-RAY DIFFRACTION TO DETECT SUBSURFACE CRYSTALLOGRAPHIC STRUCTURE

BACKGROUND OF THE INVENTION

1. Field of the Invention

This invention relates to a system and method for detecting crystallographic structures in metals. More specifically, the invention relates to a system and method for detecting surface and subsurface crystallographic grain defects in directionally solidified and single crystal castings used in gas turbines and other high temperature devices.

2. Description of the Related Art

It is known in the field of casting metal parts that directionally solidified (DS) and single crystal (SC) castings provide enhanced strength over traditional polycrystalline castings. This is primarily due to the beneficial directional grain structures and the absence of transverse grain boundaries in the castings. In the field of gas turbines, SC castings of blades and vanes have enhanced resistance to creep and low cycle fatigue compared to DS and polycrystalline castings. This is primarily due to the elimination of grain boundaries and more strengthening elements added to the SC metals.

Due to the critical nature of SC blades and vanes, these parts are inspected closely for grain defects. Some defects can cause reduced life of the part and catastrophic failure. The grain defects can be freckles, secondary grains, recrystallized grains, low and high angle boundaries, slivers, and zebras. Freckle defects are chains of equiaxed and randomly oriented grains. Secondary grains are redundant and crystallographically misoriented grains. Recrystallized grains are grains that have formed during high temperature heat treatment due to prior cold working on the part or residual stresses from casting. Low and high angle boundaries are surfaces between two misoriented grains which appear as lines of different reflective contrast. Sliver grains are narrow, elongated grains with low misorientation. Zebra grains are multiple, thin grains on platforms with low angle boundaries.

The negative effects of defects are augmented in SC parts compared to DS parts as a result of the alloying compositions of the parts. In DS alloys, elements such as zirconium, boron, and carbon are used to enhance the strength at grain boundaries, which enhances the strength of the parts. In SC alloys, zirconium, boron, and carbon are not used so that optimized heat treatment techniques can be used for enhanced part strength. However, this results in weaknesses in a SC part at the grain boundaries when grain defects do occur.

Directionally solidified parts are also sensitive to the presence of transverse grain boundaries. Grain defects, such as freckles and recrystallized grains, can significantly reduce the parts' strength.

The grain defects can be surface defects, subsurface defects, or both. It is believed that a vast majority of defects extend to the surface of a part, especially in smaller, thinner parts. Currently, surface defects can be detected by visual inspection after a surface acid etching of the part. Laue back scatter x-ray diffraction analysis has been used to determine the mismatch of crystallographic orientations and the severity of the defects and whether the part is suitable for use. The prior art discloses using an x-ray film to analyze the back scattered x-ray diffraction patterns. However, both the acid etching and using an x-ray film for back scatter diffraction analysis is time consuming and limited to surface defects, restricting its use as a tool for 100% inspection of parts.

It is also believed that some grain defects are entirely subsurface, especially for larger SC and DS parts. However, other than destructive analysis of the part, no method exists to determine the presence, location, size and degree of severity of these subsurface defects. It is possible that parts with major defects pass nondestructive inspections, including surface inspections, and are employed in turbines and other devices, which may result in part failure. Therefore, it is desirable to provide a quick system and method for detecting subsurface crystallographic grain structures and defects in a sample.

SUMMARY OF THE INVENTION

According to the invention, there is provided a sample testing system for detecting one or more crystallographic or grain structures in a sample through x-ray diffraction. The sample testing system has three parts: a testing apparatus, a computer system, and a communications line between the two. The testing apparatus has a device that emits x-rays into the sample, a device to position the sample relative to the x-rays and an electro-optical x-ray detector for detecting diffracted x-rays. The computer system has a computer, a computer program, a storage device, a database, and monitor or other means of announcing the results of a test. The computer program directs the computer to accept data from the sample testing system concerning the relationships of the devices, the x-rays, and diffracted x-rays. The computer program also directs the computer to compare this data with a database of previously determined relationships and possible diffraction patterns stored in the storage device. Based on the comparison, the computer program directs the computer to announce the results of the comparison via the monitor or other means, thereby revealing the crystallographic grain structures of the sample.

Also, according to the invention, a method positions a sample in x-rays, uses an electro-optical detector to detect x-rays diffracted by the sample, and sends this data to a computer. A computer system compares this data with a database of previously determined relationships and possible diffraction patterns. Based on the comparison, the computer system announces the results of the comparison, thereby revealing crystallographic grain structures within the sample. In another embodiment, the computer system announces the crystallographic grain structures within the sample regardless of whether the database has a direct or near comparison.

DESCRIPTION OF THE PREFERRED EMBODIMENTS

Figure 1:
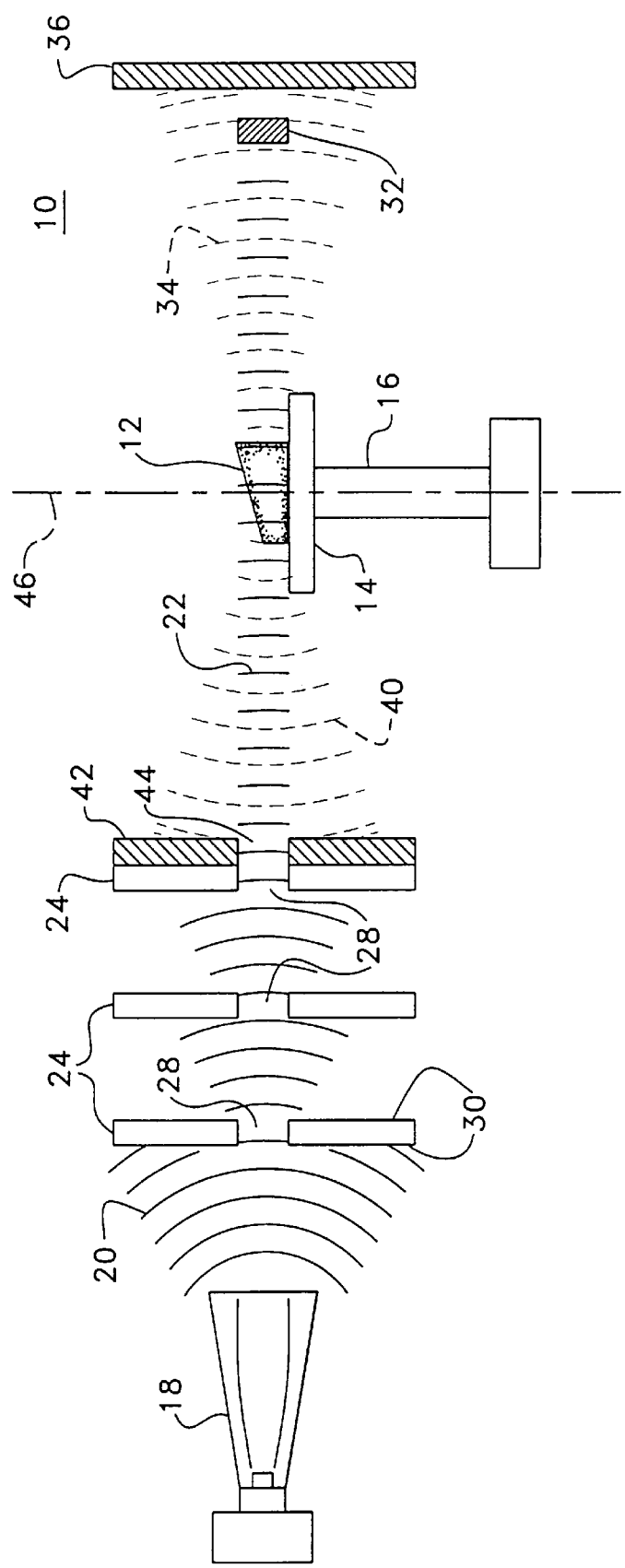
FIG. 1 shows diagrammatically a testing apparatus of the invention employing x-rays.

Referring to the drawings, wherein like numerals represent like elements, there is schematically shown in FIG. 1 a testing apparatus 10 for diffracted x-ray analysis of a sample 12. In the preferred embodiment, sample 12 is placed on a stage 14 of a positioner 16. An x-ray source 18 generates x-rays 20 which are collimated into pencil beam x-rays 22 by a series of collimators 24. Collimators 24 are disk shaped with round holes 28 extending between the circular surfaces 30 of the collimator 24. Pencil beam x-rays 22 are a narrow portion of the x-rays 20 emitted from x-ray source 18. The x-rays in the pencil beam x-rays 22 are more parallel to each other than x-rays 20 as a whole. The majority of pencil beam x-rays 22 travel directly through sample 12 and are absorbed by beam stop 32. Beam stop 32 is a disk of lead with a larger diameter than the diameter of holes 28. A minority of pencil beam x-rays 22 are not absorbed by beam stop 32 because they do not travel directly through sample 12, but are diffracted. The diffraction process is well known and is described in *Elements of X-ray Diffraction,* B. D. Cullity, 2d. ed., 1978, which is incorporated herein by reference. Some of the pencil beam x-rays 22 are diffracted slightly, becoming through transmission diffracted x-rays 34. Others pencil beam x-rays diffract backwards and become back scatter diffracted x-rays 40.

In the preferred embodiment, only through transmission diffracted x-rays 34 are analyzed. These x-rays form patterns (not shown) which can be analyzed to determine the subsurface crystallography of sample 12. In the invention, these patterns are detected by a through transmission electro-optical detector 36 depicted to the right of beam stop 32. Through transmission electro-optical detectors 36 are commercially available and include scintillators and image intensifiers. These detectors need to be large enough to detect the patterns of the through transmission diffracted x-rays 34. The detectors change the patterns into data which is used for analysis. In the invention, the patterns are sent to a computer system for analysis (See FIGS. 2 and 3).

In the preferred embodiment, x-rays 20 are broad band x-ray wavelength radiation. Broad band radiation is able to detect a wide range of crystallographic grain structures. The energy level of x-rays 20 is a trade off between diffraction measurements and penetration of sample 12. The lower the energy level, the better the detecting of the patterns. The higher the energy level, the better the penetration of sample 12 to determine subsurface crystallographic grain structures.

Other embodiments of the invention utilize narrow band wavelength radiation or fan beam x-rays. Narrow band wavelength allows for the detection of specific distances in the crystallographic planes of sample 12. Fan beams x-rays allow for the diffraction of a plane (not shown) in sample 12. This enables the analysis of sample 12 crystal by crystal.

Stage 14 is designed to hold sample 12 during the analysis. In the preferred embodiment, positioner 16 manipulates stage 14 in at least 4 degrees of freedom. The positioner vertically and horizontally moves stage 14. Additionally, the positioner 16 rotates stage 14 about a vertical axis 46. The precision required for positioner 16 is within the capabilities of commonly available commercial positioners. An aspect of the invention provides for a positioner (not shown) which tilts sample 12 by rotating stage 14 about two intersecting axes (not shown) in a horizontal plane. An additional embodiment has a static stage (not shown). Another embodiment of the invention employs a conveyor (not shown) on which is positioned the parts to be tested. The conveyor moves the parts between the collimaters and the detectors, thereby positioning each sample in pencil beam x-rays 22. This allows for quick, automated testing of multiple samples when the conveyor moves the samples into position in a series.

An embodiment of the invention analyzes back scatter diffracted x-rays 40 as well as through transmission diffraction x-rays 32. Back scatter diffracted x-rays 40 are detected in a similar manner as through transmission diffracted x-rays 34. A back scatter electro-optical detector 42 for detecting back scatter diffracted x-rays 40 is located between the series of collimators 30 and sample 12. The pencil beam x-rays 22 pass through a hole 44 in the back scatter electro-optical detector 42 and into sample 12. Some of the x-rays are diffracted backwards as back scatter diffracted x-rays 40 and strike back scatter electro-optical detector 42, which records the back scatter pattern (not shown) of the x-rays. Like the through transmission patterns, back scatter patterns are sent to a computer system for analysis (See FIGS. 2 and 3). Back scatter patterns can be analyzed for information about the crystallographic grain structure at the surface of the sample where pencil beam x-ray 22 enters sample 12. They are also used as a reference image against the pattern generated by the through transmission diffraction x-rays 32 for verifying the detected subsurface crystallographic grain structure.

Figure 2:
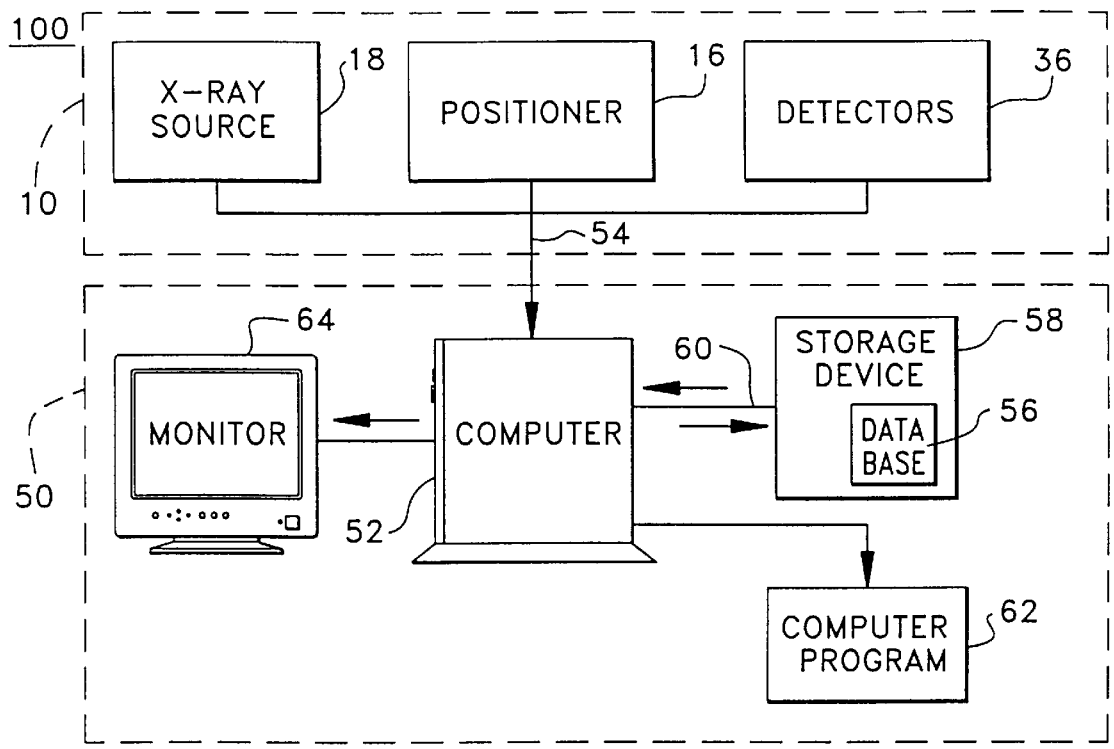
FIG. 2 shows schematically the testing apparatus, the computer system, and the communications lines between the two for an embodiment of the invention in which there is only uni-directional communication from the testing apparatus to the computer system.

Now referring to FIG. 2, sample testing system 100 is diagrammatically depicted as being comprised of testing apparatus 10 and a computer system 50. In system 100 of FIG. 2, data is transmitted only from testing apparatus 10 to computer system 50, i.e., the communications link is unidirectional. As depicted, testing apparatus 10 has x-ray source 18, positioner 16, and through transmission detector 36. Other aspects of the invention include a back scatter detector (not shown). These devices of testing apparatus 10 are also equipped to transmit sample testing data to computer system 50 via communications line 54.

Computer system 50 comprises a computer 52, a computer program 62, a storage device 58, and a monitor 64. Computer 52 receives information from testing apparatus 10 via communications line 54. Database 56, which is stored in storage device 58, contains previously determined relationships data between x-ray source 18, positioner 16, through transmission detector 36, and possible diffraction patterns of a test sample with various crystallographic grain structures. Computer 52 retrieves data from database 56 and stores testing data to the database 56 for use at another time, as shown diagrammatically at 60. All of these actions are directed by computer program 62.

Computer system 50 analyzes the data and compares it to database 56. The make-up of data in database 56 depends upon the configuration of testing apparatus 10. The relevant data to determine crystallographic grain structures are the energy and wavelengths of x-rays emitted from x-ray source 18; the location and structure of sample 12 relative to x-ray source 18; the properties of sample 12; the location of through transmission electro-optical detectors 36 and back scatter electro-optical detectors 42 (if present) relative to x-ray source 18; and the pattern of through transmission diffracted x-rays 34 and back scatter diffracted x-rays 40 detected by their respective detectors.

Database 56 will hold, at a minimum, variable information for the relevant system values that correspond to possible diffraction test patterns. The other relevant system values, the parameters, could be in database 56 or in computer program 62. In sample testing system 100, data is sent from x-ray source 18, positioner 16 and detectors 36 to computer 52. Other embodiments of the invention may not require all three devices to send information to computer 52. For example, a sample testing system (not shown) for analyzing the same type of part from only one angle using one type of x-ray would only need to send data from the detectors to computer 52 if the location of the part, positioner, x-ray device, and detectors remain the same.

Figure 3:
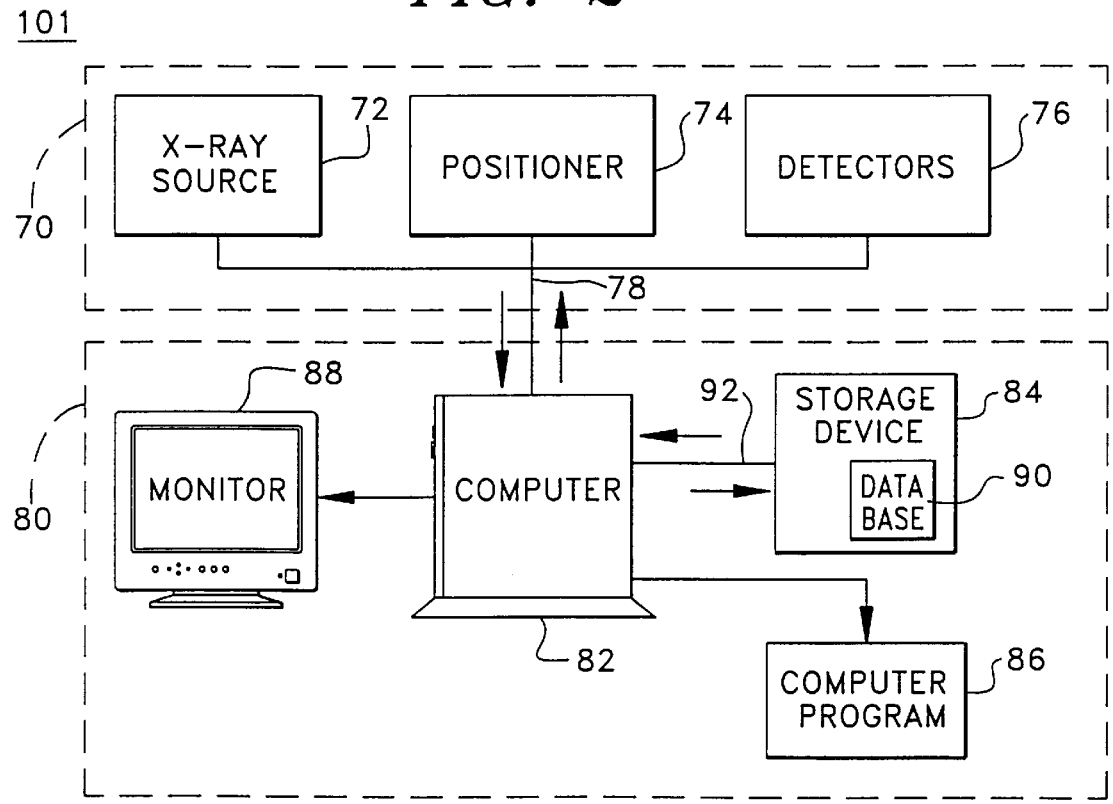
FIG. 3 shows schematically the testing apparatus, the computer system, and the communications lines between the two for an embodiment of the invention in which there is bi-directional communication between the computer system and the testing apparatus.

As shown in FIG. 3, testing apparatus 70 of sample testing system 101 has three parts which correspond to like devices of sample testing system 10: an x-ray source 72, a positioner 74, and detectors 76. Computer system 80 has a computer 82, a storage device 84, a computer program 86, and a monitor 88, which correspond to like devices in computer system 50. Database 90, which is stored in storage device 84, contains previously determined relationships data between x-ray source 72, positioner 74, detectors 76, and possible diffraction patterns of a test sample with various crystallographic grain structures. Computer 82 retrieves data from database 90, as shown diagrammatically at 92. All of these actions are directed by computer program 86.

Similar to testing apparatus 10, the devices of testing apparatus 70 send data to computer system 80 via communication lines 78. In the system 101 of FIG. 3, data is transmitted both ways between the testing apparatus 70 and computer system 80, i.e., the communications link is bi-directional. Thus, computer system 80 sends instructions to the devices of sample testing 70 via communication lines 78. X-ray device 72, positioner 74, and detectors 76 are movable at the direction of computer program 86. This allows for the testing of a sample to be automated. A user of the invention places a sample on positioner 74 and computer program 86 directs the devices within testing apparatus 70 to position the sample, emit x-rays, and record diffracted x-rays, send the relevant data to computer 82. Computer program 86 then directs computer 82 to compare the relevant data to database 90, determine the crystallographic grain structure of the sample, and announce the result. The automation within sample testing system 70 allows for quick testing of a sample. In another embodiment of the invention, computer program 86 predicts the crystallographic grain structure of the sample regardless of whether the database has a direct or near comparison.

Figure 4:
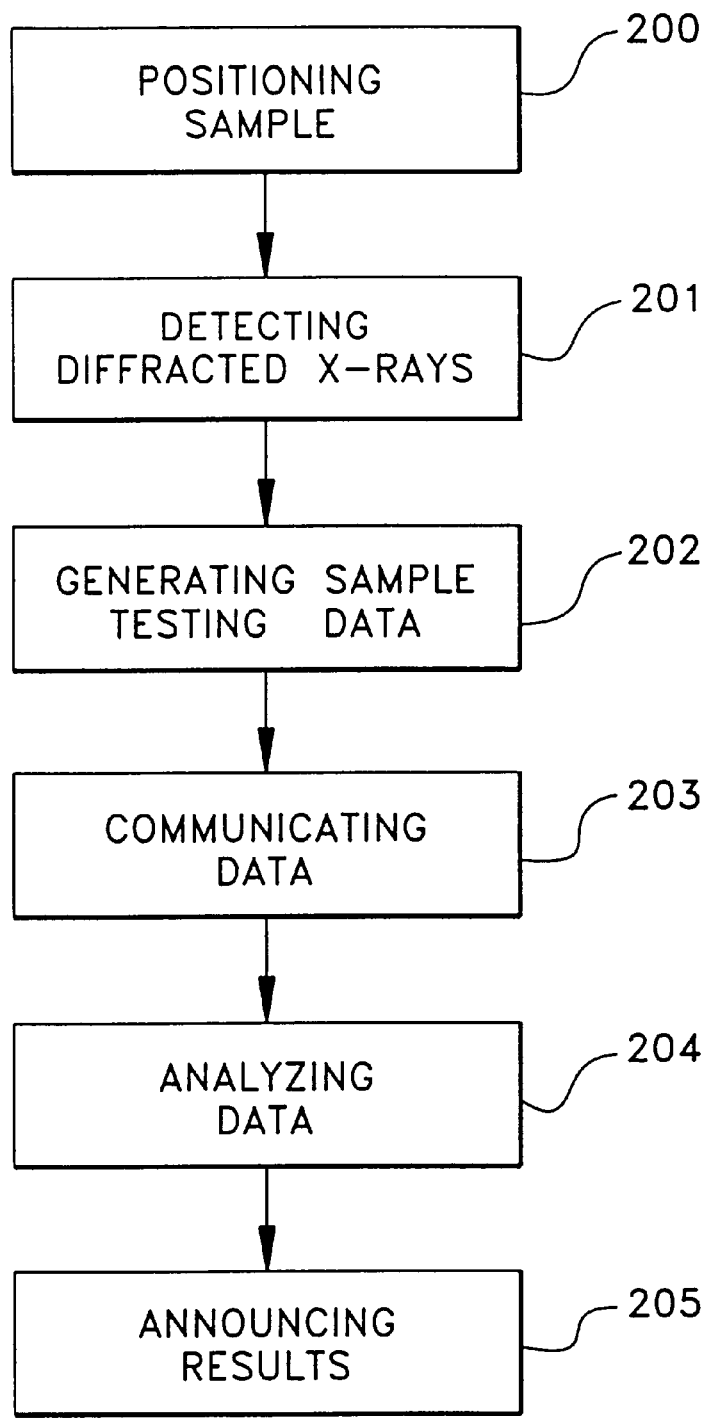
FIGS. 4 and 5 are flow charts of methods to analyze a sample using the invention.

Now referring to FIG. 4, the method for determining the crystallographic grain structure of a sample begins with positioning sample step 200, in which the sample is positioned. In sample testing system 101, the sample is placed on positioner 74, after which the computer program 86, via computer 82 and communications line 78, directs the positioner to the proper position. Next, in detecting diffracted x-rays step 201, x-ray source 72 emits x-rays, some of which are diffracted by the sample. The diffraction, which forms a pattern, is detected by detectors 76. Next, in generating sample testing data step 202, x-ray source 72, positioner source 74, and detectors 76 generate data concerning their position, strength, the pattern detected, and any other information that characterizes the system. Next, in communicating data step 203, the data generated in step 202 is sent to the computer system 80. Next, in analyzing data step 204, computer program 86 compares the sample testing data to data in database 90 that is indicative of previously determined relationship between the x-rays, the diffracted x-rays, the samples, the electro-optical detector 76, and possible diffraction patterns and determines the crystallographic grain structures of the sample. In another embodiment of the invention, analyzing step 204 determines whether or not the sample has an acceptable amount of defects. Then, in announcing results step 205, the crystallographic grain structures of the sample, based on analyzing data step 204, are announced by monitor 88. In other embodiments of the invention, a printer, a light, or an audio device is employed (not shown). Monitor 88 or a printer displays visible two dimensional or three dimensional crystallographic maps of the sample. The light is illuminated or audio device is sounded to indicate whether the sample is acceptable.

Figure 5:
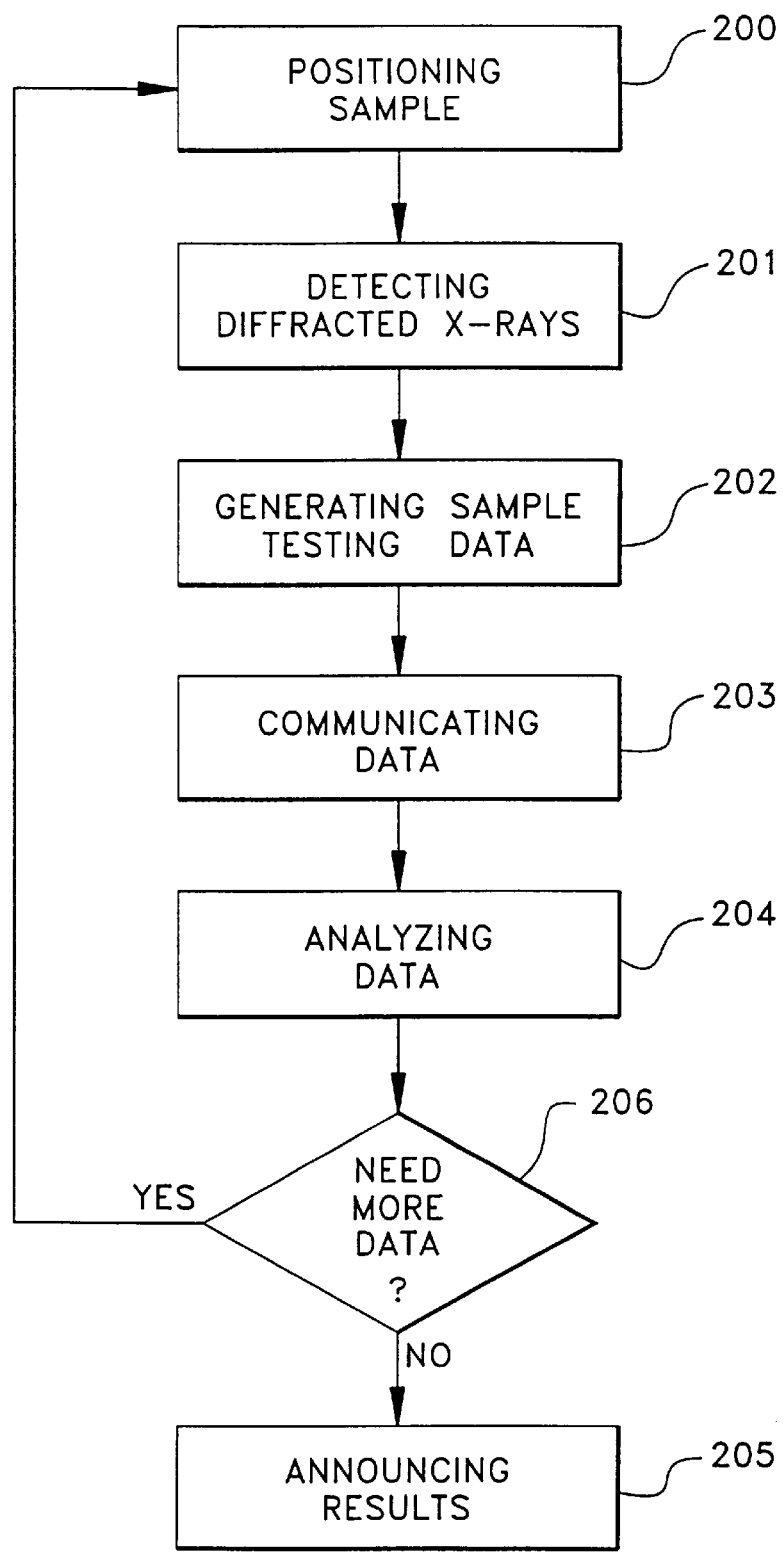

Referring to FIG. 5, an alternate method of analyzing the sample is shown. Steps 200 through 205 are performed as described previously. Additionally, there is a decision making step 206 between steps 204 and 205. The decision making step 206 tests whether more sample testing data will be required. If more sample testing data is required in analyzing step 204 to identify the crystallographic grain structure, decision making step 206 branches the method to positioning step 200. If no more sample testing data is required to determine the crystallographic grain structure, the next step is announcing results step 205. This alternate method permits computer program 62 to quickly check if the sample is SC. If it is, then announcing step 205 can announce the sample is usable. If the sample is not a SC, then the process can be repeated with a more thorough, lengthy analysis to determine if the part has a crystallographic grain structure that will permit the use of the sample. This alternate method can also be employed when a sample is required to be placed in multiple positions to be analyzed.

Any sample which has crystallographic grain structure and which x-rays can pass through can be analyzed using this invention. Additionally, the invention can be used to detect and characterize the undesirable recrystallized grains in components joined by welding, brazing, solid state bonding processes, or transient liquid phase bonding processes. Therefore, the present invention may be embodied in other specific forms without departing from the spirit or essential attributes thereof and, accordingly, reference should be made to the appended claims, rather than to the foregoing specification, as indicating the scope of the invention.

I claim:

1. A sample testing system for determining one or more subsurface crystallographic grain structures in a sample comprising:
   a) a testing apparatus comprising:
      i) x-ray means for projecting broadband x-rays into the sample;
      ii) sample positioning means for positioning the sample in the x-rays; and
      iii) through transmission detector means comprising an electro-optical detector for detecting through transmission x-ray diffraction patterns generated by the x-rays after passing through and being diffracted by the sample and generating through transmission detector means data including subsurface crystal defect data;
   b) communication means for communicating sample testing data comprising the through transmission detector means data to a computer system; and
   c) wherein the computer system comprises:
      i) analyzing means for determining subsurface crystal defects of the sample by comparing the sample testing data to data indicative of a previously determined relationship between the x-ray means, the sample positioning means, the through transmission detector means, and possible diffraction patterns thereof, and
      ii) announcing means for announcing the subsurface crystal defects of the sample.

2. The system of claim 1, further comprising:
   back scatter x-ray detector means for detecting back scatter x-ray diffraction patterns generated by the x-rays diffracted by the sample and generating back scatter detector means data, comprising an electro-optical detector;
   wherein the sample testing data further comprises the back scatter detector means data; and wherein the analyzing means further compares the sample testing data to the data indicative of previously determined relationship between the back scatter detection means and the possible diffraction patterns.

3. The system of claim 1, wherein:

the x-ray means further comprises means for generating x-ray means data; and sample testing data further comprises the x-ray means data.

4. The system of claim 1, wherein:

the sample positioning means further comprises a stage for holding the sample, the stage being movable relative to the x-ray means vertically and horizontally, and being rotatable about a vertical axis, and means for generating sample positioning means data; and the sample testing data further comprises the sample positioning means data.

5. The system of claim 4, wherein the stage is rotatable about two intersecting axes in a horizontal plane.

6. The system of claim 1, wherein the sample positioning means further comprises a conveyor.

7. The system of claim 1, wherein the analyzing means comprises a database of data indicative of a previously determined relationship between the x-ray means, the sample positioning means, the through transmission detector means, and the possible diffraction patterns, and a computer program for directing the computer system to analyze the sample testing data against the data in the database.

8. The system of claim 7, wherein:

the sample positioning means is movable by the computer system.

9. The system of claim 1, wherein the analyzing means comprises a computer program which analyses the sample testing data and determines crystallographic grain structures.

10. The system of claim 1, wherein the announcing means generates one of:

a visible two dimensional crystallographic map of the sample;

a visible three dimensional crystallographic map of the sample;

an illumination; or a sound.

11. A method for determining one or more subsurface crystallographic grain structures of a sample comprising the steps of:

positioning the sample in a path of broadband x-rays projecting from an x-ray means;

detecting x-rays that pass through and are diffracted by the sample, defining through transmission diffracted x-rays, with at least one electro-optical detector;

generating and communicating sample testing data concerning the x-rays, the through transmission diffracted x-rays, the electro-optical detector, and the sample to a computer system;

analyzing the sample testing data to determine the subsurface crystal defects of the sample by comparing the sample testing data to data indicative of a previously determined relationship between the x-rays, the through transmission diffracted x-rays, the samples, the electro-optical detector, and possible diffraction patterns; and announcing the subsurface crystal defects of the sample based on the analyzing step.

12. The method of claim 11, wherein the detecting step comprises detecting back scatter x-ray diffraction patterns.

13. The method of claim 11, wherein the announcing step comprises employing the computer system to generate one of:

a visible two dimensional crystallographic map of the sample; or a visible three dimensional crystallographic map of the sample;

an illumination; or a sound.

14. The method of claim 12, wherein the positioning step comprises placing the sample on a stage movable relative to x-rays vertically and horizontally, and being rotatable about a vertical axis, and positioning the sample by moving the stage.

15. The method of claim 12, wherein the positioning step comprises a conveyor moving the sample into the path of the x-rays.

16. The method of claim 11, wherein the analyzing step comprises employing a database of the previously determined relationships data between the x-rays, the diffracted x-rays, the electro-optical detector, and the sample, and possible diffraction patterns, and a computer program for directing the computer system to analyze the sample testing data against the database.

17. The method of claim 16, wherein the positioning step comprises employing the computer system to position the sample.

18. The method of claim 11, wherein the analyzing step comprises employing a computer program which analyses the sample testing data and determines crystallographic grain structures.

* * * * *